US00PP20304P2

(12) United States Plant Patent
Talmadge

(10) Patent No.: US PP20,304 P2
(45) Date of Patent: Sep. 15, 2009

(54) ***NEMESIA* PLANT NAMED 'BALARWITIM'**

(50) Latin Name: *Nemesia foetans*
Varietal Denomination: Balarwitim

(75) Inventor: Paul A. Talmadge, Orcutt, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/218,443

(22) Filed: Jul. 15, 2008

(51) Int. Cl.
*A01H 5/00* (2006.01)

(52) U.S. Cl. ..... Plt./458
(58) Field of Classification Search ..... Plt./458
See application file for complete search history.

(56) References Cited

PUBLICATIONS

Canada Plant Breeders'Rights Application No. 08–6201 filed Feb. 28, 2008. Published information from web site attached http://www.inspection.gc.ca.

*Primary Examiner*—Kent L Bell
(74) *Attorney, Agent, or Firm*—Audrey Charles

(57) ABSTRACT

A new and distinct cultivar of *Nemesia* plant named 'Balarwitim', characterized by its white-colored flowers, medium green-colored foliage, and moderately vigorous, mounded growth habit.

1 Drawing Sheet

Latin name of genus and species of plant claimed: *Nemesia foetans.*
Variety denomination: 'Balarwitim'.

BACKGROUND OF THE INVENTION

The present invention relates to a new and distinct cultivar of *Nemesia* plant botanically known as *Nemesia foetans* and hereinafter referred to by the cultivar name 'Balarwitim'.

The new cultivar originated in a controlled breeding program in Guadalupe, Calif. during October 2005. The objective of the breeding program was the development of *Nemesia* cultivars that are freely flowering with unique flower coloration and a well-branched, compact growth habit.

The new *Nemesia* cultivar is the result of open-pollination. The female (seed) parent of the new cultivar is the proprietary *Nemesia foetans* breeding selection designated 5291-3, not patented, characterized by its white-colored flowers, medium green-colored foliage, and moderately vigorous, mounded growth habit. The male (pollen) parent of the new cultivar is unknown. The new cultivar was discovered and selected as a single flowering plant within the progeny of the above stated open-pollination during March 2006 in a controlled environment at Guadalupe, Calif.

Asexual reproduction of the new cultivar by terminal stem cuttings since March 2006 at Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balarwitim' as a new and distinct cultivar of *Nemesia* plant:

1. White-colored flowers;
2. Medium green-colored foliage; and
3. Moderately vigorous, mounded growth habit.

Plants of the new cultivar differ from plants of the female parent primarily in flower size and branching characteristic. The new cultivar has larger flowers and more branches than the female parent.

Of the many commercially available *Nemesia* cultivars, the most similar in comparison to the new cultivar is Vanilla Sachet 'Pensug', U.S. Plant Pat. No. 12,811. However, in side by side comparisons, plants of the new cultivar differ from plants of 'Pensug' in at least the following characteristics:

1. Plants of the new cultivar have larger flowers than plants of 'Pensug';
2. Plants of the new cultivar have wider inflorescences than plants of 'Pensug'; and
3. Plants of the new cultivar are wider than plants of 'Pensug'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balarwitim'. The plants were grown in 4.5 inch pots for 7 weeks in a greenhouse at West Chicago, Ill.

DETAILED BOTANICAL DESCRIPTION

Figure 1:
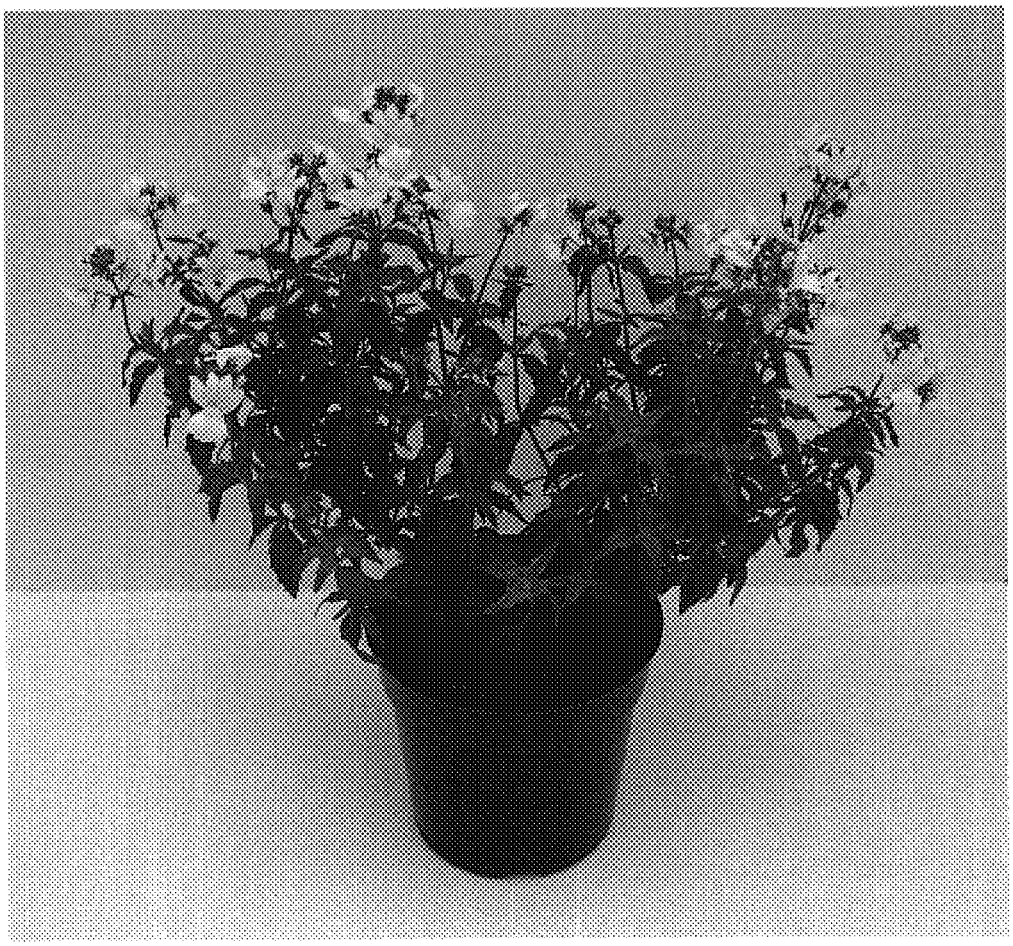
FIG. 1 illustrates a side view of the overall growth and flowering habit of 'Balarwitim'.
Figure 2:
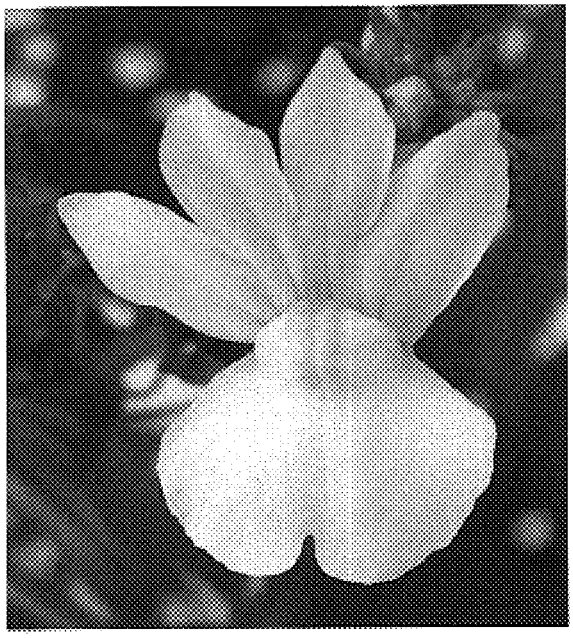
FIG. 2 illustrates a close-up view of an individual flower of 'Balarwitim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 30, 2008 between 1:00 p.m. and 3:00 p.m. under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Nemesia foetans* cultivar Balarwitim.

Parentage:

*Female parent.*—Proprietary *Nemesia foetans* breeding selection designated 5291-3, not patented.

*Male parent.*—Unknown.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fine, white in color.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, mounded growth habit.

*Size.*—Height from soil level to top of plant plane: Approximately 16.6 cm. Width: Approximately 26.5 cm.

*Branching habit.*—Freely branching. Pinching enhances lateral branching. Quantity of main branches per plant: 6.

*Branch.*—Shape: Square in cross section. Strength: Moderate, flexible. Length: Approximately 20.1 cm. Diameter: Approximately 2.5 mm. Length of central internode: Approximately 1.9 cm. Texture: Glabrous. Color of young and mature stems: 144A.

Foliage description:

*General description.*—Quantity of leaves per branch: Approximately 14. Fragrance: None. Form: Simple. Arrangement: Opposite.

*Leaves.*—Aspect: Perpendicular to obtuse angle to stem. Shape: Ovate. Margin: Widely serrate. Apex: Acute. Base: Broadly attenuate. Venation pattern: Pinnate. Length of mature leaf: Approximately 2.5 cm. Width of mature leaf: Approximately 1.3 cm. Texture of upper surface: Glabrous. Texture of lower surface: Glabrous. Color of upper surface of young foliage: 144A with slightly darker venation. Color of lower surface of young foliage: 144B with venation of 144A. Color of upper surface of mature foliage: 137A with slightly darker venation. Color of lower surface of mature foliage: 138B with venation of 138A.

*Petiole.*—Length: Approximately 2.0 mm. Diameter: Approximately 1.0 mm. Texture: Glabrous. Color: 137C.

Flowering description:

*Flowering habit.*—'Balarwitim' is freely flowering under outdoor growing conditions with substantially continuous blooming from spring through autumn and year round in greenhouse environment.

*Lastingness of individual bloom.*—Approximately 4 to 6 days.

Inflorescence description:

*General description.*—Type: Terminal raceme. Flowers face upright and outwardly. Flowers not persistent. Quantity per plant: Approximately 17. Fragrance: Strong, honeysuckle-like. Length or height: Approximately 6.4 cm. Width: Approximately 3.7 cm. Quantity of fully open flowers per inflorescence: Approximately 4.

*Peduncle.*—Shape: Square in cross section. Strength: Strong. Aspect: Erect. Length: Approximately 2.9 cm. Diameter: Approximately 1.5 mm. Texture: Glabrous. Color: 144A.

Flower description:

*Type.*—Solitary, zygomorphic.

*Bud.*—Rate of opening: Generally takes 2 to 3 days for bud to progress from first color to fully open flower.

*Bud just before opening.*—Shape: Ovoid with spur. Length, including spur: Approximately 1.0 cm. Diameter: Approximately 5.0 mm. Texture: Sparsely glandular pubescent. Color: Closest to 145D.

*Corolla.*—Shape: Bilabiate with nectar spur. Flower has five petals; four upper petals are fused at base to form an upright lobed and arched banner lip; the fifth lower petal is modified into a larger lip with nectar spur. Width: Approximately 1.7 cm. Length: Approximately 2.0 cm. Depth: Approximately 1.2 cm.

*Upper lip.*—Shape: Oval to oblanceolate. Margin: Entire. Apex: Rounded. Length of central lobes from throat: Approximately 1.0 cm. Width of central lobes: Approximately 3.0 mm. Length of lateral lobes from throat: Approximately 8.0 mm. Width of lateral lobes: Approximately 4.0 mm. Texture of upper and lower surfaces: Glabrous. Color of upper and lower surfaces when fully open: Purer white than 155D.

*Lower lip.*—Shape: Obovate. Margin: Entire, undulate. Apex: Emarginate. Length from palate: Approximately 7.5 mm. Width: Approximately 1.2 cm. Texture of upper and lower surfaces: Glabrous. Color of upper and lower surfaces when fully open: Purer white than 155D. Palate length: Approximately 2.0 mm. Palate width: Approximately 2.0 mm. Palate color: 2A with glandular pubescence of 2b and 172A. Throat length: Approximately 4.0 mm. Throat width: Approximately 4.0 mm. Throat texture: Glandular pubescent. Gland color: A mixture of colorless, 2C and 172A. Throat color: Purer white than 155D with a central area of 2C.

*Nectar spur.*—Length: Approximately 4.0 mm. Diameter at proximal end: Approximately 1.0 mm. Diameter at distal end: Less than 1 mm. Texture: Glabrous. Color: Closest to 145D.

*Calyx.*—Shape: Star. Diameter: Approximately 7.0 mm.

*Sepals.*—Quantity per flower: 5, fused at base. Shape: Narrow elliptic. Apex: Acute. Length: Approximately 4.0 mm. Width: Approximately 1.0 mm. Texture of upper and lower surfaces: Sparsely glandular pubescent. Color of upper and lower surfaces: 144A at base transitioning to 137A at apex.

*Pedicel.*—Strength: Strong, flexible. Aspect: At an acute angle. Length: Approximately 9.0 mm. Diameter: Less than 1 mm. Texture: Glandular pubescent. Color: 144A.

*Reproductive organs.*—Androecium: Stamen quantity: 4 per flower, didynamous. Filament length of longer pair: Approximately 3.0 mm. Filament length of shorter pair: Approximately 1.0 mm. Filament color: 155D, translucent. Anther shape: Bilobed, ovoid. Anther length: Less than 1 mm. Anther color: 11B. Pollen amount: Abundant. Pollen color: 11C. Gynoecium: Pistil quantity: 1 per flower. Pistil length: Approximately 2.0 mm. Stigma shape: Rounded. Stigma color: 145D. Style length: Approximately 1.0 mm. Style color: 155D, translucent. Ovary length: Approximately 1.0 mm. Ovary texture: Glabrous. Ovary color: 145A.

Seed and fruit production: Neither seed nor fruit production has been observed.

Disease and pest resistance: Resistance to pathogens and pests common to *Nemesia* has not been observed.

What is claimed is:

1. A new and distinct cultivar of *Nemesia* plant named 'Balarwitim', substantially as herein shown and described.

* * * * *